United States Patent
Cully

(10) Patent No.: US 10,675,162 B2
(45) Date of Patent: Jun. 9, 2020

(54) POST-IMPLANTATION CONTRACTIBLE OR EXPANDABLE DEVICES AND METHOD OF USING AND MAKING THE SAME

(71) Applicant: W. L. Gore & Associates, Inc., Newark, DE (US)

(72) Inventor: Edward H. Cully, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 255 days.

(21) Appl. No.: 15/852,808

(22) Filed: Dec. 22, 2017

(65) Prior Publication Data

US 2018/0116831 A1  May 3, 2018

Related U.S. Application Data

(62) Division of application No. 14/066,365, filed on Oct. 29, 2013, now Pat. No. 9,883,956.

(60) Provisional application No. 61/720,875, filed on Oct. 31, 2012.

(51) Int. Cl.
| | |
|---|---|
| *A61F 2/06* | (2013.01) |
| *A61F 2/852* | (2013.01) |
| *A61L 31/14* | (2006.01) |
| *A61B 17/12* | (2006.01) |
| *A61L 31/02* | (2006.01) |
| *A61B 17/00* | (2006.01) |

(52) U.S. Cl.
CPC ............ *A61F 2/852* (2013.01); *A61B 17/12* (2013.01); *A61L 31/022* (2013.01); *A61L 31/148* (2013.01); *A61B 2017/00004* (2013.01); *A61B 2017/00867* (2013.01); *A61F 2210/0004* (2013.01); *A61F 2210/0014* (2013.01); *A61F 2210/0076* (2013.01); *A61F 2310/00017* (2013.01)

(58) Field of Classification Search
CPC ...... A61F 2/06; A61F 2/07; A61F 2/82; A61F 2/852; A61F 2210/0004; A61F 2210/0014
See application file for complete search history.

(56) References Cited

U.S. PATENT DOCUMENTS

| | | | |
|---|---|---|---|
| 5,667,523 | A | 9/1997 | Bynon et al. |
| 6,350,277 | B1 | 2/2002 | Kocur |
| 6,878,160 | B2 | 4/2005 | Gilligan |
| 2010/0241214 | A1 | 9/2010 | Holzer |
| 2010/0262221 | A1 | 10/2010 | Schafer |
| 2010/0268317 | A1 | 10/2010 | Stiger |

*Primary Examiner* — Melanie R Tyson

(57) ABSTRACT

Devices and methods for the controlled over-expansion of a body conduit and controlled constriction or expansion of a vessel in a patient are described. In various embodiments, a device includes a bio-corrodible expandable support structure and an implant coaxially adjacent the support structure. Contraction of the implant can occur when the support structure is bioabsorbed.

17 Claims, 7 Drawing Sheets

POST-IMPLANTATION CONTRACTIBLE OR EXPANDABLE DEVICES AND METHOD OF USING AND MAKING THE SAME

CROSS-REFERENCE TO RELATED APPLICATION

This application is a divisional of U.S. patent application Ser. No. 14/066,365, filed Oct. 29, 2013, which claims the benefit of U.S. Provisional Application 61/720,875, filed Oct. 31, 2012, both of which are incorporated herein by reference in their entireties for all purposes.

FIELD

The present disclosure relates in general to medical devices and more particularly to medical devices designed to at least partially corrode away in the body.

BACKGROUND

Medical devices are frequently used to treat the anatomy of patients. Such devices can be permanently or semi-permanently implanted in the anatomy to provide treatment to the patient. Endoluminal devices, such as for example stents, grafts, stent-grafts, filters, valves, occluders, markers, and therapeutic agent delivery devices, are inserted into the body at an insertion point and moved through a lumen to a treatment area using a catheter. Exoluminal devices, such as for example clips, rings, snares, staples, grafts, therapeutic agent delivery devices and the like, are inserted into a body cavity and implanted surgically or inserted and moved to a treatment site using an endoscopic tool. Exoluminal devices for repair or restriction of a body conduit, such as for example dilation or diameter restrictors, constrictors, cuffs, anastamoses, venous valve supports, devices for repairing arteriovenous malformations and trauma damage, and exo-vascular stents, can be fastened around the outside of the vessel at the repair site.

Medical devices such as exoluminal and endoluminal devices can be made partially or entirely of materials that are designed to degrade in the human body. In some instances, a medical device is needed only temporarily in the human body, and it can be more practical to design a device to degrade rather than try to remove it from the patient when it is no longer needed. For example, a medical device used to provide temporary support for a body conduit can be made from bio-corrodible metals, biodegradable polymers, or combinations of these materials. When such an implant partially or wholly disappears in vivo, it is said to have bio-corroded or biodegraded, or that it was absorbed by the body. The degradation products generated from the bio-corroding or biodegrading device can be biocompatible.

Although many advances have been made to medical devices in general, the deployment of an exoluminal or endoluminal medical device can be limited in range or stages of expansion or contraction or be too invasive for a particular therapy. Such deployment can be inherent to the design of a medical device. Additionally, a medical device can not have any ability to change its configuration, such as its physical dimensions, in the patient over time to address the patient's changing physiology or to provide a delayed or extended therapeutic procedure.

Therefore, new medical devices that are amenable to slow and controlled remodeling, or that change in configuration over extended periods of time in the patient, are desired.

SUMMARY

Expandable devices, such as stents or stent-grafts, are used in a variety of endoluminal procedures in the human body to repair aneurysms and to support various anatomical lumens, such as blood vessels, respiratory ducts, gastrointestinal ducts, and the like. Expandable devices can have a reduced diameter when in a collapsed configuration, and an expanded diameter once located at the treatment site in the patient. Expandable devices can be constrained in the collapsed configuration to facilitate transport to the treatment site. Expandable (endoluminal) devices can have a first, constricted diameter, and then have an expanded diameter when forced into an expanded configuration, and then will re-assume a neutral state diameter once located at the treatment site in the patient and the expansive force is removed. Contractible (exoluminal) devices, such as exo-vascular stents for aneurysm repair, can be constricted and placed over a vessel and configured to resume an expanded neutral state configuration once the constricting force has been removed

BRIEF DESCRIPTION OF THE DRAWINGS

The accompanying drawings are included to provide a further understanding of the disclosure and are incorporated in and constitute a part of this specification, illustrate embodiments of the disclosure, and together with the description serve to explain the principles of the disclosure, wherein.

DETAILED DESCRIPTION OF THE ILLUSTRATED EMBODIMENTS

Figure 1:
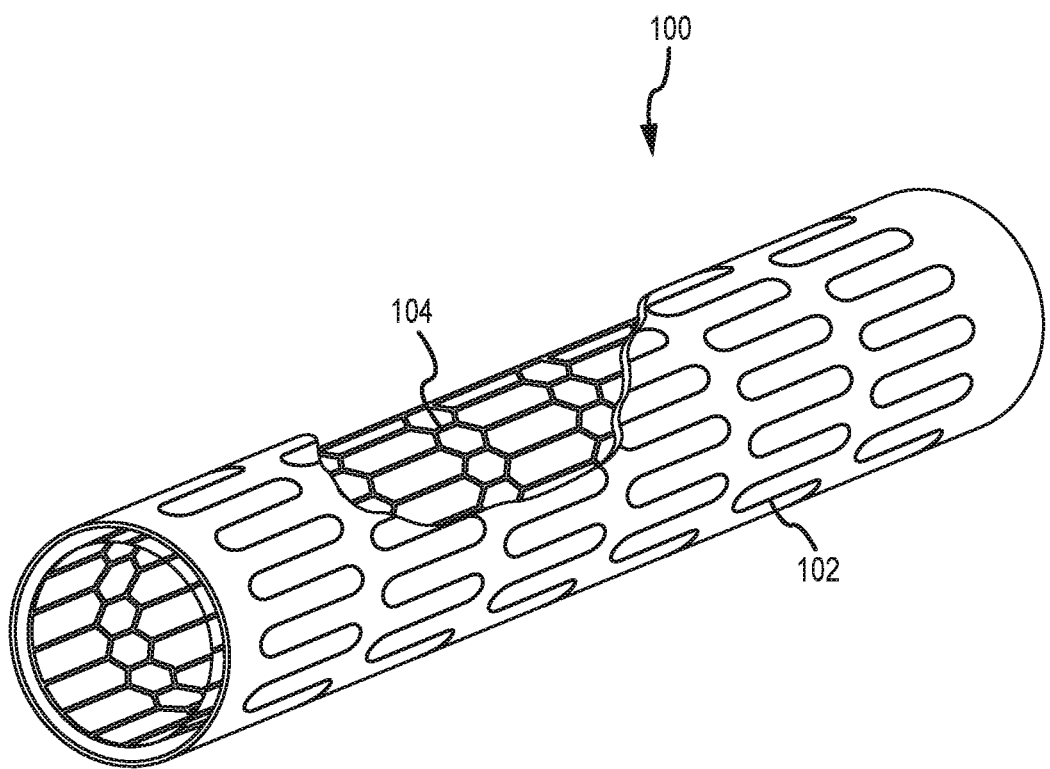
FIG. 1 illustrates a perspective view of an embodiment of a device in accordance with the present disclosure.

Persons skilled in the art will readily appreciate that various aspects of the present disclosure can be realized by any number of methods and systems configured to perform the intended functions. Stated differently, other methods and systems can be incorporated herein to perform the intended functions. It should also be noted that the accompanying figures referred to herein are not all drawn to scale, but are exaggerated to illustrate various aspects of the present disclosure, and in that regard, the drawing figures should not be construed as limiting.

With that said, and as will be described in more detail herein, various embodiments of the present disclosure generally comprise expandable medical devices having the capability to be over-expanded and to controllably contract back to a neutral state as a support structure bio-corrodes away over time. Various other embodiments of the present disclosure generally comprise a contractible medical device having the capability to progressively constrict a body conduit over time as a support structure within the device bio-corrodes away. Conversely, various other embodiments of the present disclosure generally comprise an expandable medical device having the capability to expand a body conduit as a support structure within the device bio-corrodes away over time. Various other embodiments of the present disclosure generally comprise methods to maintain a device in an over-expanded configuration within a lumen for an approximate, predetermined period of time, and methods to maintain an exoluminal device in a constricted or expanded configuration around the outside of a lumen for an approximate, predetermined period of time.

As used herein, "bio-corrodible" means the ability for the metallic portions of a medical device to absorb, resorb, corrode, fracture, dissolve, degrade, and/or disintegrate partially or fully over time while residing inside a patient and when exposed to physiological fluids, electrolytes and dissolved gasses such as hydrogen ions, chloride ions, sodium ions, potassium ions, bicarbonate, phosphate, blood, lymph, proteins, amino acids, plasma, oxygen, carbon dioxide, and the like. Bio-corrosion can involve any combination of metal corrosion processes such as galvanic, pit, crevice, intra-granular, inter-granular, stress-corrosion cracking, corrosion fatigue, fretting corrosion, and the like. Bio-corrosion can comprise any combination and degree of uniform and non-uniform disintegration, for example with accelerated or decelerated zones of corrosion, longitudinally aligned corrosion, varying ratios of inter- to intra-grain corrosion, varying degrees of fragmentation of the device or elements of the device, and further corrosion of the fragments. The bio-corrosion of a medical device can include various stages of structural breakdown of portions of the device or the entire device.

As used herein, the term "neutral state" refers to the configuration at which an elastic implantable device is manufactured in. Whether the device is deformed to an undersized or oversized condition, or extended or compressed axially, this device will tend toward its neutral state. During implantation, such tendency toward the neutral state can aid in the remodel of tissue.

As used herein, "biodegradable" means the ability for a medical device comprising polymeric components to hydrolyzes, fractures, corrodes, degrades, dissolves, absorbs, resorbs, disintegrates, or otherwise assimilates into the body partially or fully over time while residing inside a patient and when exposed to a physiological environment, which can include water, electrolytes and dissolved gasses such as hydrogen ions, chloride ions, sodium ions, potassium ions, bicarbonate, phosphate, blood, lymph, proteins, amino acids, plasma, oxygen, carbon dioxide, and the like. For example, organic polymers such as polyesters can degrade in vivo by chemical transformations such as hydrolysis or oxidation.

As used herein, "bioabsorbable," refers to a material that can be biodegradable and/or bio-corrodible as defined herein. In other words, it can comprise bio-corrodible elements, biodegradable elements, or both.

As used herein, "medical devices" can include, for example, stents, grafts, stent-grafts, filters, valves, occluders, markers, sensors, therapeutic agent delivery devices, prostheses, pumps, bandages, clips, snares, staples, dilation restrictors, constrictors, cuffs, anastamoses, venous valve supports, devices for repairing arteriovenous malformations and trauma damage, and other implantable devices, whether exoluminal and endoluminal, that are implanted, temporarily or chronically, in the vasculature (vessel) or other body lumen, or implanted within a body cavity around the outside of a vessel or other body lumen, at a treatment region or site. Such medical devices can comprise a flexible material that can provide a fluid-resistant or fluid-proof surface, such as a vessel bypass or blood occlusion. A medical device or a portion of a device that is implantable can be referred to as an implant.

As used herein, a "medical device assembly" means the combination of a medical device and at least one other component that facilitates the insertion, movement, deployment or other action of the medical device. For example, a balloon catheter can be combined with a medical device such as a stent-graft to complete a medical device assembly.

As used herein, the term "constrain" can mean (i) to limit expansion, be it self-expansion or expansion assisted by a device, of the diameter of an implant, or (ii) to cover or surround, but not otherwise restrain, an implant (e.g., for storage or biocompatibility reasons and/or to provide protection to the implant and/or the vasculature).

As used herein, "contractible implant" is the term used for an elastic endoluminal or exoluminal device which is manufactured at a known diameter, which herein is referred to as the neutral diameter. The expandable implant may be held temporarily in a dilated state by a plastically deformable or shape memory bioabsorbable support structure. The contractible device will tend to return to its neutral state when the internal support structure is bioabsorbed.

In some embodiments, the contractible implant is capable of being constrained in profile, allowing it to be remotely delivered in an endoluminal fashion. A contractible implant can be capable of dilation to an over-expanded deformed diameter by a balloon or by release from a constraining mechanism. A "contractible implant" can include, for example, any medical device suitable for delivery to the treatment site at a delivery diameter, and at least a portion of the implant can be capable of dilation from the delivery diameter up to a diameter or a range of diameters greater than the neutral diameter, up to a predetermined maximum diameter.

The diameter of the device at a neutral state can depend on the function of the device. Regardless of function, at least a portion of a contractible implant can have a particular diameter or dimension where the device is in a neutral state, and a smaller or larger configuration obtained through deformation of that portion. In various embodiments, at a neutral diameter, which is greater than the delivery profile of an endoluminal implant, the diameter of the implant can be the desired ultimate diameter of a vessel as a result of the treatment. In other embodiments, at a neutral state, the neutral diameter of at least a portion of the length of a contractible implant can be less than the diameter of the vessel as a result of the treatment. For example, a proximal or distal end of a device can have a neutral diameter slightly less than the vessel to be treated to provide a mode of device retrieval.

For endoluminal device, in an over-dilated configuration, the device or a portion thereof can provide a frictional fit or mechanical anchoring within a vessel. In an embodiment, an over-dilated configuration can be larger than or approximately the same size as the vessel to be treated. In some instances, temporarily or only slightly over-expanding the vessel can be beneficial, e.g., to provide a temporary larger vessel or to facilitate tissue in-growth into the endothelial layers of the lumen. In other instances, the over-dilated configuration is configured to engage an over-dilated vessel, so that tissue in growth can occur and then subsequent contraction of the implant can also contract the vessel. Such expandable devices can include, for example, stents, grafts, and combinations thereof.

In various embodiments, a contractible implant can comprise a radially collapsed configuration suitable for delivery to the treatment area of the vasculature of a patient. Such a contractible implant can be constrained in a radially collapsed configuration and mounted onto a delivery device such as a catheter. The diameter of the contractible implant in the collapsed configuration is preferably small enough for the implant to be guided through the vasculature and delivered to the treatment area. In various embodiments, the diameter of the collapsed configuration is small enough to minimize the crossing profile of a catheter and reduce tissue damage to the patient. In various embodiments, a collapsed configuration can represent a deformed state for the implant relative to an expanded configuration.

In various embodiments, a contractible implant can comprise a shape memory material, such as a self-expanding stent or stent-graft. Generally, self-expanding devices dilate from a radially collapsed deformed configuration to a radially expanded neutral configuration when unconstrained. In the present disclosure, a contractible implant can be capable of an assisted over-expansion beyond its neutral configuration with the aid of a secondary, bioabsorbable support structure. A contractible implant can comprise a shape memory alloy or polymer, so that the contractible implant contracts from an over-expanded configuration to an undeformed, neutral configuration as the supporting structure is bioabsorbed. The shape memory material used for the contractible implant can include, for example, a copper based or Ni—Ti (Nitinol) based alloy, and the implant can be capable of a one-way or two-way memory effect. In an embodiment, a device can comprise an outer surface, e.g., the outer surface of the expandable implant that promotes tissue in growth, which can have utility in vessel remodeling and/or facilitating bioabsorption.

In various other embodiments, the support structure is a plastically deformable structure and thus a balloon can be used to expand the contractible implant to an over-expanded state. In other embodiments, the support structure is constructed of a shape memory material wherein the neutral diameter is greater than the neutral diameter of the contractible implant. Combinations of support structures can also be utilized to tailor the stages contraction.

Similarly, for exoluminal devices, the contractible implant can be placed around a vessel in an over-expanded state with the aid of a secondary, bioabsorbable support structure. As the support structure is bioabsorbed, the implant will contract and ultimately constrict, partially or completely, and/or remodel the circumscribed vessel.

As used herein, "expandable implant" is the term used for an elastic, shape memory exoluminal device which is manufactured at a known diameter, which herein is referred to as the neutral diameter. The expandable implant is capable of being reduced in size and applied to the outer surface of an organ or vessel. The expandable implant may be held temporarily in an under-sized state by a plastically deformable or shape memory bioabsorbable, secondary support. The expandable implant will tend to return to its neutral state when the constraining force of the secondary support is removed. An "expandable implant" can include, for example, any medical device suitable for application to the exoluminal treatment site and the implant or a portion thereof can be capable of expansion from the diameter of the initial implantation profile, through a range of intermediary enlarged diameters, up to a predetermined "neutral" diameter. As with the contractible implant, the expandable implant can have a particular diameter or range of diameters across its length where the device is relatively undeformed. In various embodiments, an expandable implant can be relatively deformed when the diameter of the implant is small enough to contact a vessel to be treated. In various embodiments, an expandable implant can be expanded to its undeformed diameter that is larger than the diameter of a vessel to be treated upon removal or degradation of the constraining, support structure. In an embodiment, an expandable implant can be configured to be side-mounted on to a vessel, e.g., by comprising a discontinuous section and/or an interlocking junction along its length.

In an embodiment, described devices can comprise an inner or outer surface that promotes tissue in growth, which can have utility in vessel remodeling and/or facilitating bioabsorption.

In various embodiments, an expandable implant or a contractible implant can comprise a stent or stent-graft. Stent-grafts are designed to generally comprise one or more stent elements that form a support structure, with one or more graft members placed over and/or under the stent. Stent elements can include, for example, struts, wires, ribbons, rings, or tubes. Stent elements can comprise wire wound into sinusoidal and/or undulating pattern(s).

In various embodiments, graft materials in stent-grafts can include polymeric and/or natural or biologically derived materials. The graft can be biodegradable polymer and/or promote tissue in growth. Polymeric grafts include expanded polytetrafluoroethylene (ePTFE), polyester, polyurethane, fluoropolymers, such as perfluoroelastomers and the like, polytetrafluoroethylene, silicones, urethanes, ultra high molecular weight polyethylene, polyethylenes such as Dacron®, aramid fibers, and combinations thereof. Other embodiments for a graft member material can include high strength polymer fibers such as ultra-high molecular weight polyethylene fibers (e.g., Spectra®, Dyneema Purity®, etc.) or aramid fibers (e.g., Technora®, etc.). Biologically derived materials include bovine arteries/veins, pericardium, subintestinal submucosa, and collagen. The graft member can be treated, coated, or imbibed with a bioactive agent. Any graft member that can be delivered in a patient to a treatment site is in accordance with the present disclosure.

In various embodiments, the outer surface of described endoluminal devices can comprise a layer that allows for tissue in growth. Or conversely, the inner surface of an exoluminal device can comprise a layer that allows for tissue in-growth. Facilitating in-growth permits the graft member to be incorporated into the vessel wall after a period of time. In an embodiment, the exterior surface of graft member 104 can comprise a material that has an open, porous microstructure. An open microstructure provides an uneven surface topography having crevices, tunnels, and cavernous features within which cells and tissue(s) can occupy. Similarly, in other embodiments, the exterior surface can comprise an open macrostructure which can facilitate tissue in-growth, e.g., a surface providing a lattice framework that provides an uneven surface topography with surface features within which cells and tissue(s) can occupy. In addition, the outer surface can be coated or treated with beneficial agents that enhance the rate of tissue in growth. For example, in an embodiment, a beneficial agent can comprise a pro-angeogenic agent, such as a vascular endothelial growth factor.

In various embodiments, the support structure of a stent or stent-graft can comprise, for example, a plurality of stent elements physically connected, whether directly or indirectly, to one another into an integrated stent structure for coordinated movement, such as radial expansion and/or contraction and longitudinal and/or radial compliancy. Stent elements can also be connected together for additive strength in holding open a vessel or constricting closed a vessel. An integrated stent structure can comprise woven or wrapped wires or a cut metal tube. Interconnected, integrated structures can be obtained by cutting away material in a pattern from a tube using a laser.

For cooperative movement and additive support, stent rings or struts, for example, can be operatively coupled to one another with a wire, a weld, adhesives, or other suitable connector. A wire used to couple stent ring elements can attach to the peak of a first stent ring and a valley of a second stent ring. The stent ring can be arranged such that the peaks and valleys are in-phase (e.g., the peaks of the first stent ring share a common centerline with the peaks of the second stent ring) or out of phase (e.g., the peaks of the first stent ring share a common centerline with the valleys of the second stent ring). Alternatively, some or all of the stent elements can be physically separate from one another, being only associated with one another through disposition on the same graft or catheter. Any expandable or contractible stent component configuration that can be delivered to a treatment site is contemplated by the present disclosure.

Stent elements used for expandable structures or contractible structures can be formed from metallic, polymeric, or natural materials. Said materials can be bioabsorbable. For example, metallic materials can include suitable biocompatible metal or metal alloy, such as iron, magnesium, zinc, tungsten, or an alloy of thereof Polymeric materials include both homopolymers and copolymers, which can in whole or in part include, for example, nylons, polyacrylamides, polycarbonates, polyethylenes, polyformaldehyde, polymethylmethacrylates, polypropylenes, polytetrafluoroethylene, polytrifluorochlorethylene, polyvinylchloride, polyurethanes and elastomeric organosilicon polymers, and can include organic materials absorbed by the body such as poly(amino acids), poly(anhydrides), and the hydrolysable polyesters, such as poly(caprolactones), poly(lactic/glycolic acid), poly(hydroxybutyrates) and poly(orthoesters). The material can be an elastic material, e.g., Nitinol, and the like.

Natural materials can include biologically derived materials such as bovine arteries/veins, pericardium, subintestinal submucosa, and collagen.

In various embodiments, medical device components, such as stent elements, comprise an iron alloy. An iron alloy refers to a metal composition with iron (Fe) present as the major component. In various embodiments, an iron alloy can comprise at least 50% iron. In various embodiments, an iron alloy can comprise at least 60% iron. In various embodiments, an iron alloy can comprise at least 70% iron. In various embodiments, an iron alloy can comprise at least 80% iron. In various embodiments, an iron alloy can comprise at least about 90% iron. In various embodiments, an iron alloy can comprise at least about 95% iron. In addition to the elemental iron, iron alloys for use in bio-corrodible medical devices can comprise non-iron elements such as carbon, nickel, cobalt, manganese, magnesium, lithium, calcium, chromium, molybdenum, tantalum, platinum, palladium, vanadium, iridium, rhenium, rhodium, rubidium, osmium, tungsten, titanium, niobium, zirconium, hafnium, aluminum, boron, sulfur, tin, silicon, yttrium, zinc, bismuth, silver, copper, iridium, indium, tin, and any lanthanide or actinide. In various embodiments, an iron alloy for a medical device designed to corrode in the body can comprise from 0 to about 40% manganese, 0 to about 5% chromium, 0 to about 10% nickel, 0 to about 25% cobalt, 0 to about 1% aluminum, 0 to about 5% molybdenum, 0 to about 3% titanium, 0 to about 3% zirconium, 0 to about 1% carbon, 0 to about 1% silicon, 0 to about 3% niobium, 0 to about 1% nitrogen, and 0 to about 1% yttrium, with the remainder iron. Examples of iron alloys for use in bio-corrodible medical devices in accordance with the present disclosure can be found in U.S. Pat. No. 8,246,762 to Janko et al., the content of which is incorporated herein by reference in its entirety.

In various embodiments, an iron alloy for use in accordance with the present disclosure can comprise any structural form. For example, the iron alloy can comprise any amounts of ferrite, martensitic, austenitic, cementite, pearlite, or bainite forms, or amorphous forms. If crystals are present in the iron alloy, the resulting grains can be of any size from ultrafine (sub-micron scale) to large (hundreds of micron scale), and orientated in any direction or multiple directions. If present, grains can be deformed to become columnar as the result of directional elongation and orientation. In various embodiments the iron alloy in accordance with the present disclosure can be polycrystalline or single crystal in form.

In various embodiments, an implant such as an expandable or contractible stent-graft can be constrained by a "sleeve," which circumferentially surrounds the implant. In various embodiments, a sleeve circumferentially surrounds an endoluminal implant and constrains it in a delivery configuration. In various embodiments, a sleeve circumferentially surrounds a shape memory implant, preventing the implant from self-expanding until the sleeve is removed. In other embodiments, a sleeve circumferentially surrounds an implant to protect the device and tissue from damage as the device is transferred through a body cavity to a treatment site in the patient.

As used herein, "deployment" refers to the actuation of a medical device at a treatment site, such as, the removal of a sleeve on a shape memory implant to allow the implant to expand or the expansion of an expandable member, such as a balloon, to plastically deform an implant. The implant can be deployed to its initial, under or over sized configuration to achieve a desired therapeutic outcome, such as tissue in-growth. The implant can then contract or expand to its neutral state at a later time to achieve a desired therapeutic outcome. Examples of constraining members and coupling members for releasably maintaining expandable devices in a delivery configuration for endoluminal delivery can be found in U.S. Pat. No. 6,352,561 to Leopold et al., the content of which is incorporated herein by reference in its entirety.

In various embodiments in accordance with the present disclosure, a medical device comprises an expandable bioabsorbable support structure disposed on at least a portion of the inner or outer surface of a contractible implant, wherein the bioabsorbable support structure can comprise a corrodible metal alloy or biodegradable polymer. In various embodiments, the contractible implant can be a shape memory material. In various embodiments, the support structure is also a shape memory structure that can be self-expanding (with a static diameter different from the static diameter of the contractible implant), or it can be inelastic and require assisted expansion, e.g., balloon expanded. In various embodiments, both the contractible implant and the support structure are tubular in shape and in a coaxial, circumscribing arrangement resembling a "tube inside a tube." In various embodiments, the support structure at its initial delivery profile can serve to constrain the contractible implant to the delivery profile. In various embodiments, the coaxially arranged components can be mounted onto a balloon of a balloon catheter as a medical device assembly used for delivery of endoluminal devices. In various embodiments, both the contractible implant and the support structure can be collapsed down to a delivery profile and constrained in a constraining sleeve. In various embodiments, at least one of the support structure and the contractible implant can comprise a stent or a stent-graft. As previously described, in various embodiments, the support structure can be built at a delivery profile diameter and balloon expanded to an over-expanded diameter. In other embodiments, the support structure can be self-expandable, constructed at a diameter different from, e.g., greater than, the static diameter of the contractible implant.

In various embodiments, a device in accordance with the present disclosure comprises an expandable, bioabsorbable support structure made from a bio-corrodible metal alloy or a biodegradable polymer and having a delivery diameter configured to obtain an expanded, supporting diameter, and a contractible implant, at least a portion of which coaxially surrounds or underlies the bioabsorbable support structure, with the implant having a collapsed deformed diameter, a neutral, intermediate diameter, and an over-expanded deformed diameter. In various embodiments, the delivery diameter of the support structure can be approximately equal to the collapsed deformed diameter of the implant. In various embodiments, the over-expanded deformed diameter of the implant can be approximately equal to the supporting diameter of the support structure. In various embodiments, the coaxially arranged support structure and contractible implant can expand as a single device. For example, a balloon inside the support structure can be used to expand the support structure from a delivery diameter up to a supporting diameter, and since at least a portion of the expandable implant surrounds the support structure or is attached to the inner surface thereof, it too expands from the collapsed deformed diameter up to the over-expanded deformed diameter. Once the forces used to expand the device in this manner are removed, such as removal of the balloon, the expanded support structure functions as the structure holding the outer implant in its over-expanded configuration. In various embodiments, bioabsorption of the support structure results in a loss of the ability for the support structure to hold at least a portion of the expandable implant in an over-expanded state, resulting in eventual contraction of the over-expanded section.

In various embodiments, a device in accordance with the present disclosure comprises an support structure made from a bio-corrodible metal alloy or biodegradable polymer, having a diameter, and a contractible implant; at least a portion of which is coaxially disposed about or below the bio-corrodible support structure, having an over-expanded, deformed diameter substantially equal to the diameter of the support structure and a neutral diameter less than the diameter of the support structure. Prior to bioabsorption, the contractible implant diameter generally corresponds to the diameter of the support structure. In various embodiments, the device can be placed around a vessel in contact with the vessel wall. Similar to the above embodiment, bioabsorption of the support structure results in a loss of the ability for the support structure to hold at least a portion of the expandable implant in an over-expanded state, resulting in eventual contraction of the over-expanded section to the neutral diameter.

In various embodiments, a device in accordance with the present disclosure comprises a support structure made from a bio-corrodible metal alloy or biodegradable polymer, having a diameter, and an expandable implant; at least a portion of which is coaxially disposed about or below the bio-corrodible support structure. The implant comprises a contracted, deformed diameter substantially equal to the diameter of the support structure and a neutral diameter greater than the diameter of the support structure. Prior to bioabsorption, the expandable implant diameter generally corresponds to the diameter of the support structure. In various embodiments, the device can be placed around a vessel in contact with the vessel wall, optionally, at least partially or completely constricting. Similar to the above, bioabsorption of the support structure results in a loss of the ability for the support structure to deform at least a portion of the expandable implant in under-sized, constrained state, resulting in eventual expansion of the constrained section to the neutral diameter. In various embodiments, the inner surface can comprise a layer that facilitates tissue in-growth, facilitating vessel remodeling, because the vessel will radially expand along with the expandable implant.

In various embodiments, the design of the implant can at least in part determine the rate at which the implant will self-contract or self-expand from an over or under-sized diameter to the neutral configuration by memory as the support structure is bioabsorbed. Bioabsorption of the support structure may not be uniform, and as parts of the structure are bioabsorbed, portions of the over-expanded implant adjacent these bioabsorbed sites will eventually and/or progressively contract or expand, while other portions of the implant surrounding stable regions of the support structure can remain over or under-sized.

Eventually, the entire support structure will be absorbed and the under or over-sized sections of the implant will eventually expand or contract, returning to the neutral diameter. The manner of contraction can be tailored at least in part by the design of the implant and/or support structure. For example, a support structure in the form of a stent-type design can be configured to bioabsorb in a desired manner. Stent design features, such as individual stent strut weight, length, thickness, arrangement, and material type, can be varied to tailor the rate and/or manner at which the implant will contract/expand as the support structure bioabsorbs. In various embodiments, in order to tailor the manner or rate of contraction/expansion the support structure comprises a non-shape memory material, shape memory material, or combinations thereof. For example, the bioabsorbable support structure can comprise a first structure that facilitates an over-expanded diameter layered with a second structure comprising a shape memory material that facilitates a diameter in between the over-expanded diameter and the neutral diameter of the implant. Additional layers of support structures can be used to increase the number of incremental, contracting diameters.

In various embodiments, at least one of the expandable, bioabsorbable support structure and the implant coaxially disposed about or under the support structure comprise a stent or stent-graft. For example, in various embodiments an inner support structure comprises a stent whereas an outer implant comprises a stent-graft, or vice versa. In various embodiments, both the support structure and the implant comprise stent-grafts. In various embodiments each comprises a stent. In various other embodiments, the outer support structure comprises a stent-graft and the inner implant comprises a stent, or vice versa.

In various embodiments, the expandable support structure and implant, at least a portion of which is coaxially disposed about or under the support structure are physically coupled together, whether in a discontinuous or continuous manner. In an embodiment, the implant and the support structure can be coupled, via a weld or adhesive, at a plurality of sites evenly dispersed along the length and circumference. As discussed, both the support structure and the implant can comprise stent grafts. Graft material present on each component can be fused together by thermal bonding and/or by adhesives. For example, graft material on both the expandable support structure and the implant can comprise expanded polytetrafluoroethylene (ePTFE), optionally coated with an adhesive such as for example fluoroethylene propylene (FEP). With the support structure and implant bonded together, prior to significant bioabsorption, the diameter of the support structure will correlate to the diameter of the implant. For example, self-expansion or balloon expansion of the support structure will necessarily expand the coaxially arranged implant to its over-expanded diameter.

In various embodiments, a device comprises an expandable support structure and an expandable or contractible implant coaxially adjacent the support structure, wherein the support structure comprises a non-shape memory alloy. In various embodiments, the expandable support structure comprises an iron alloy having greater than at least one of about 50% iron, about 60% iron, about 70% iron, about 80% iron, about 90% iron, and about 95% iron. In various embodiments, the inner support structure is fabricated from a metal alloy comprising from 0 to about 40% manganese; 0 to about 5% chromium; 0 to about 10% nickel; 0 to about 25% cobalt; 0 to about 1% aluminum; 0 to about 5% molybdenum; 0 to about 3% titanium; 0 to about 3% zirconium; 0 to about 1% carbon; 0 to about 1% silicon; 0 to about 3% niobium; 0 to about 1% nitrogen; and 0 to about 1% yttrium, with the remainder being iron.

In various embodiments, optionally, the implant portion of the device can also be capable of bio-corroding and/or biodegrading within the body. The bioabsorption rate of the support structure can be faster than the bioabsorption rate of the implant such that the support structure is absorbed first, resulting in the contraction of the over-expanded implant, and then the implant eventually is bioabsorbed over a longer timeframe. In various embodiments, the implant is a stent or stent-graft comprising a bio-corrodible iron alloy.

In various embodiments, in accordance with the present disclosure, the device comprising an expandable support structure and an implant coaxially disposed about or under the support structure can be an exoluminal device. As discussed, an exoluminal device is a medical device implanted on the outside of a body conduit. An example of an exoluminal device in accordance with the present disclosure is an exovascular stent, which can be used, e.g., to facilitate fistula maturation in an A-V fistula. An exoluminal device can be applied to a body conduit in need of treatment. In various embodiments, the device can be tubular and can require interlocking junction along its length. Or alternatively, a body conduit can be detached and reattached at some point such that the device can be slipped over the conduit.

In various embodiments, in accordance with the present disclosure, an exoluminal device can comprise a support structure coaxially disposed along at least a portion of contractible/expandable implant, wherein both the support structure and the implant are substantially tubular in shape, with the support structure coaxially adjacent the implant. As tubular structures, both the support structure and the implant have generally circular openings at each end, and the ends of the tubular implant may or may not line up with the ends of the tubular support structure.

In various embodiments, a discontinuous section or interlocking junction running the length of an exoluminal device facilitates the wrapping of the device around the outside of a body conduit without detaching the conduit at some point in the body. In this way the device can be opened along the discontinuous section or interlocking junction and positioned around the conduit in need of treatment. In an embodiment, the device positioned around a conduit can then be secured with at least one suture to join the longitudinal edges of the device. Depending on the particular device and treatment, the longitudinal edges of the device can be stitched together with a plurality of suture stitches. In various embodiments, said sutures can be bioabsorbable.

In various embodiments, a method for maintaining an implant in an over-expanded state in a lumen for a predetermined period of time comprises: locating in a lumen a device comprising a bio-corrodible support structure and a contractible implant coaxially adjacent the support structure; expanding the support structure from its delivery diameter to an expanded supporting diameter with concomitant radial expansion of the implant from its collapsed deformed diameter to an over-expanded deformed diameter; and, allowing the support structure to be bioabsorbed over a approximated, predetermined period of time, resulting in the implant obtaining its neutral configuration. The period of time during which the lumen remains in an over-expanded state can be determined by the rate of bio-corrosion of the expanded support structure in the body when exposed to physiological fluids and dissolved gasses in vivo. In various embodiments the bio-corrosion rate can be investigated in vitro and in vivo, and changes to the design of the expandable support structure can be made to adjust the time predicted for bioabsorption of the support structure within the body. In an embodiment, the time frame at which the implant is over-expanded can be sufficient to permit tissue in-growth into an outer layer of the device, so that as the implant radially contracts, the vessel wall radially contracts as well.

In various embodiments, in accordance with the present disclosure, a method for constricting a lumen at a time subsequent to implantation comprises locating on a lumen an exoluminal device comprising a support structure and a contractible implant coaxially adjacent the support structure and allowing the support structure to at least one of bio-corrode and biodegrade over an approximated, predetermined period of time. The time frame when the device begins to radially contract is determined by the bioabsorption rate of the support structure when exposed to physiological fluids and dissolved gasses in vivo. In various embodiments, the bioabsorption rate can be investigated in vitro and in vivo, and changes to the design and/or material of the support structure can be made to adjust the time predicted for bioabsorption of the alloy into the body.

In various embodiments, in accordance with the present disclosure, a method for radially expanding a lumen at a time subsequent to implantation comprises locating on a lumen an exoluminal device comprising a support structure and an expandable implant coaxially adjacent the support structure and allowing the support structure to at least one of bio-corrode and biodegrade over an approximated, predetermined period of time. The time frame when the device begins to radially expand is determined by the bioabsorption rate of the support structure when exposed to physiological fluids and dissolved gasses in vivo. In various embodiments, the bioabsorption rate can be investigated in vitro and in vivo, and changes to the design and/or material of the support structure can be made to adjust the time predicted for bioabsorption of the alloy into the body. In an embodiment, the time frame at which the expandable implant is constricted can be sufficient to permit tissue in-growth into an inner layer of the device, so that as the implant radially expands, the vessel wall radially expands as well.

In various embodiments, the device used in the method for maintaining an implant in a constricted state on a vessel comprises an expandable implant having a constricted deformed diameter and a larger, neutral diameter that the implant will expand to by memory when left unsupported. In various embodiments, the expanded undeformed diameter of the implant is approximately equal to or greater than the diameter of the conduit to be treated.

In various embodiments, in accordance with the present disclosure, such an expandable implant as discussed above can be located on the adventitia of a vessel within the vasculature of a patient, optionally constricting the vessel partially or completely. Bioabsorption of the support structure allows the expandable implant to expand the vessel in the patient after sufficient cellular in-growth has occurred.

In various embodiments in accordance with the present disclosure, a method for the controlled expansion of a vessel in a patient comprises locating on a vessel a device comprising a support structure and an expandable implant coaxially surrounding the support structure and allowing the support structure to bioabsorb over an approximated predetermined period of time.

In various embodiments, in accordance with the present disclosure, a method of dilating a vessel comprises locating a device having a support structure coaxially adjacent a expandable implant in a starting (constricted) configuration around an exterior portion of a vessel, and allowing the support structure to bioabsorb over time causing expansion of the implant from a constricted deformed diameter to an expanded undeformed diameter.

The above being noted, with reference now to FIG. 1, a medical device 100 in accordance with the present disclosure is illustrated. Device 100 comprises a generally tubular shaped support structure 104 and a generally tubular shaped contractible implant 102, coaxially arranged. The cutaway view provided in FIG. 1 reveals that the support structure 104 is directly inside and in physical contact with the implant 102. Either structure 104 or implant 102 can comprise a stent or stent-graft. When implant 102 is a stent-graft, the radio-transparency of the graft material can affect how visible the supporting structure 104 is through the implant 102. In various embodiments, support structure 104 is expandable with the assistance of a secondary device. In other embodiments, support structure 104 is a shape memory material that facilitates expansion of implant 102 to an over-expanded diameter. Implant 102 can be similarly constructed of a shape memory material and obtains its neutral configuration upon bioabsorption of the support structure 104. The supporting structure 104 can be coupled in any manner to the implant 102 can hold the contractible implant 102 in an over-expanded state. For example, both structure 104 and implant 102 can comprise a stent that share a common graft. For example, device 100 can be constructed by the sequential addition of materials, such as tape, film, and tubular shaped integrated stent structures such as wire scaffolds, onto a cylindrical mandrel, with heat applied to soften, melt, and bond layers of material together. When supporting structure 104 is bonded to the inner or outer circumference of the contractible implant 102, the supporting structure 104 can hold the implant 102 in an over-expanded diameter. In other embodiments, the supporting structure 104 and the implant 102 are merely coupled by an interference fit within the host vessel.

In some embodiments, assisted radial expansion of the device by expansion of a balloon coaxially inside structure 104 will result in the expansion of both structures 104 and implant 102 together. Support structure 104 prevents the contractible implant 102 from obtaining its neutral state, e.g., spontaneously contracting to a neutral diameter when over-expanded. Thus, in various embodiments, in order for a contractible implant 102 to contract in diameter, the supporting structure 104 is bioabsorbed to the point it can no longer supports implant 102.

Figure 2:
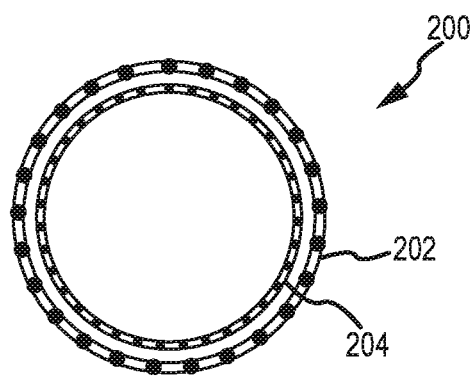
FIG. 2 illustrates a cross-sectional view of an embodiment of a device in accordance with the present disclosure.

Referring now to FIG. 2, a cross-section of the medical device 200 in accordance with the present disclosure is illustrated. Device 200 comprises a supporting structure 204 and a contractible implant 202, coaxially adjacent. In this cross-sectional view, both components of the device are seen to be substantially circular in cross-section, with the implant 202 circumferentially disposed around the inner supporting structure 204. In various embodiments, there can be a friction fit between the outer wall of the inner support structure 204 and the inner wall of the outer implant 202. In various embodiments, the structure 204 and the implant 202 can be indirectly coupled, e.g., at least partially filled with graft material and/or various adhesives.

Figures 3A, 3B, 3C:
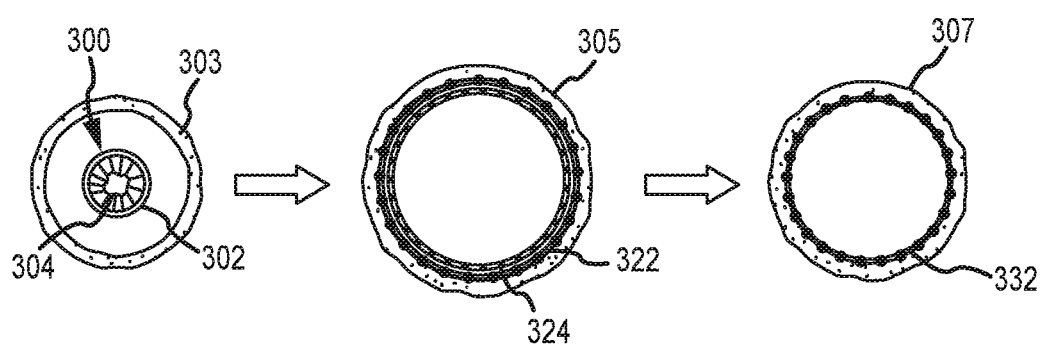
FIG. 3A illustrates a cross-sectional view of an embodiment of a device in accordance with the present disclosure in a delivery profile.
FIG. 3B illustrates a cross-sectional view of an embodiment of a device in accordance with the present disclosure in an over-expanded configuration.
FIG. 3C illustrates a cross-sectional view of an embodiment of an expanded implant in a lumen in accordance with the present disclosure.

Referring now to FIG. 3A, the cross-section of an endoluminal device 300 in accordance with the present disclosure is illustrated. The device 300 is illustrated in a delivery profile coaxially inside a lumen 303. The supporting structure 304 and the contractible implant 302, in coaxial relationship and having substantially circular cross-sections. In the delivery configuration for the device 300 as illustrated, the supporting structure 304 can comprise a delivery diameter, and the contractible implant 302 can comprise a collapsed deformed diameter. The contractible implant 302 comprises a shape memory material and having a neutral configuration/diameter. Supporting structure 304 can be self-expandable or expandable with a secondary device and capable of expansion to at least the diameter greater than the neutral diameter, so that the contractible implant 302 is in an over-expanded deformed configuration.

Referring now to FIG. 3B, the device of the present disclosure is illustrated in the over-expanded configuration, providing a treatment to the lumen 305. The coaxially arranged supporting structure 324 is expanded and the contractible implant 322 is over-expanded, the result for example of balloon-assisted concerted expansion of structure 324 and implant 322. Balloon assisted over-expansion can be used to force the lumen 305 radially out to an over-expanded diameter as illustrated. Upon removal of the balloon or other expansion device, the structure 324 holds the contractible implant 322 in an over-expanded state. The implant 322 comprises a shape memory construct, made at least in part from a shape memory material, such as Nitinol, trained to return to a smaller, neutral diameter if left unsupported. During this temporary over-expansion phase, the expanded supporting structure 324 can hold the implant 322 radially outward and firmly against the wall of the over-expanded vessel, preventing the over-expanded implant 322 from returning to the neutral diameter.

In some embodiments, temporary over-expansion of the device within the lumen can help to embed the outer implant 322 into the wall of the lumen 305. In an embodiment, the exterior surface of the implant 322 comprises an exterior layer which permits tissue in growth. Corrosion and structural breakdown of the inner supporting structure 324 allows the over-expanded implant 322 to return to the smaller neutral diameter by action of the shape memory material, as discussed herein, bringing the vessel down to a desired diameter.

Referring now to FIG. 3C, bio absorption of the supporting structure (324 in FIG. 3B) allows the over-expanded contractible implant (322 in FIG. 3B) to contract to its neutral configuration 332 and facilitate the vessel (305 in FIG. 3B) to also contract. Implant 332 can remain at least partly embedded in the wall of the lumen 307 as shown. As discussed above, contractible implant 332 can begin with a diameter substantially matching the diameter of the untreated vessel (such as an aneurysm), and upon bio-absorption of the support structure 334, contractible implant 332 can contract to a more normal vessel diameter 307. In further embodiments, implant 332 can also be at least partially bioabsorbable, and it can eventually be bioabsorbed.

In various embodiments, in accordance with the present disclosure, a method of maintaining a lumen in an over-expanded state uses a device comprising a contractible implant and a supporting structure designed to absorb over an approximate, predetermined time period. To temporarily maintain a vessel in an over-expanded state, the device is transferred to the treatment site on a balloon catheter and over-expanded when properly located. Over an approximated, predetermined period of time, the supporting structure degrades or corrodes to the point; it can no longer retain the contractible implant in an over-expanded state, allowing the temporarily over-expanded implant with shape memory to contract to its neutral state. Thus, a method for treating a lumen includes a temporary over-expansion of an implant, with the method comprising: (1) delivery of a device comprising a contractible implant as described and supporting structure at a delivery diameter, $d^1$; (2) self-expansion of the supporting structure and implant or assisted over-expansion of both the implant and supporting structure to an over-expanded diameter $d^3$; and (3) contraction of the implant to its neutral diameter $d^2$ upon bioabsorption of the inner supporting structure.

Figure 4:
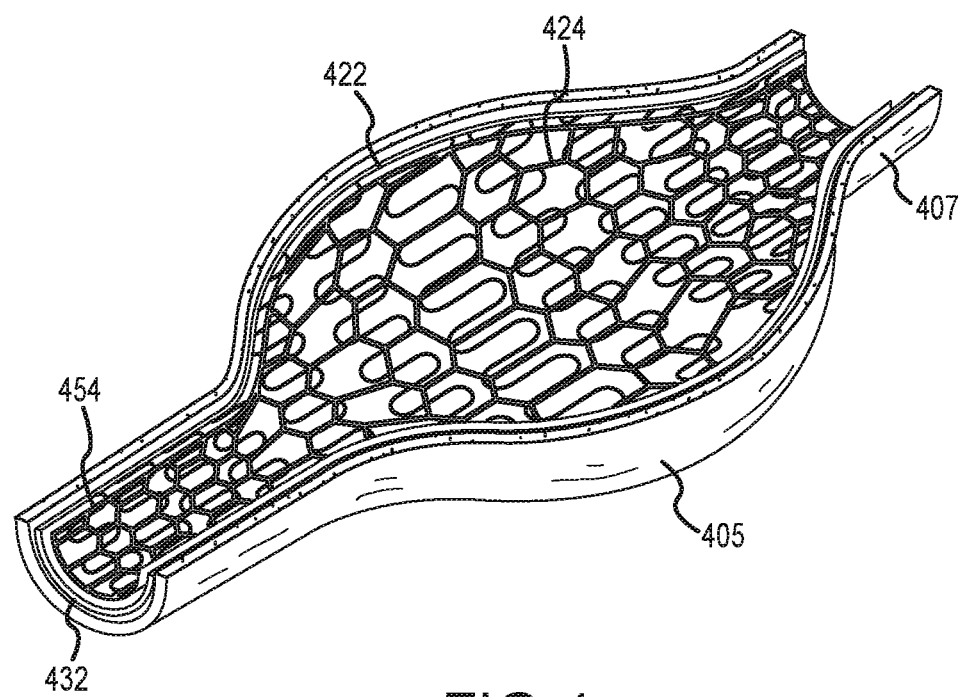
FIG. 4 illustrates a cross-sectional perspective view of an embodiment of an over-expanded lumen in accordance with the present disclosure.

With reference now to FIG. 4, a cut away perspective view of an implanted device in accordance with the present disclosure is illustrated. Vessel 407 is over-expanded in region 405, with the over-expanded portion 422 of the contractible implant 432 held against the wall of the vessel by the supporting structure 424. In this embodiment, in the region of the vessel not over-expanded, the implant 432 remains at a neutral diameter, which can be more comparable to the normal size of the vessel 407 or slightly larger to provide a mechanical fit of the implant 432 in the normal sized vessel 407. As illustrated, supporting structure 424 is adjacent the lumen and implant 422 is positionable against the vessel wall. In the over-expanded state, the implant 422 can be pressing against the wall of the vessel in the over-expanded region 405. The treatment illustrated in FIG. 4 can include a temporary over-expansion of vessel 407 which can facilitate cellular in-growth into the implant 422, and/or to allow a temporary vasodilation of the vessel for some therapeutic purpose. The bioabsorption of supporting structure 424 will result in the contraction of the over-expanded implant 422 back to neutral diameter such as found in the portion 432 of the implant. Since implant 422 is now connected to the vessel 405, contraction of the implant 422 will tend to pull vessel 405 with it.

Figure 5:
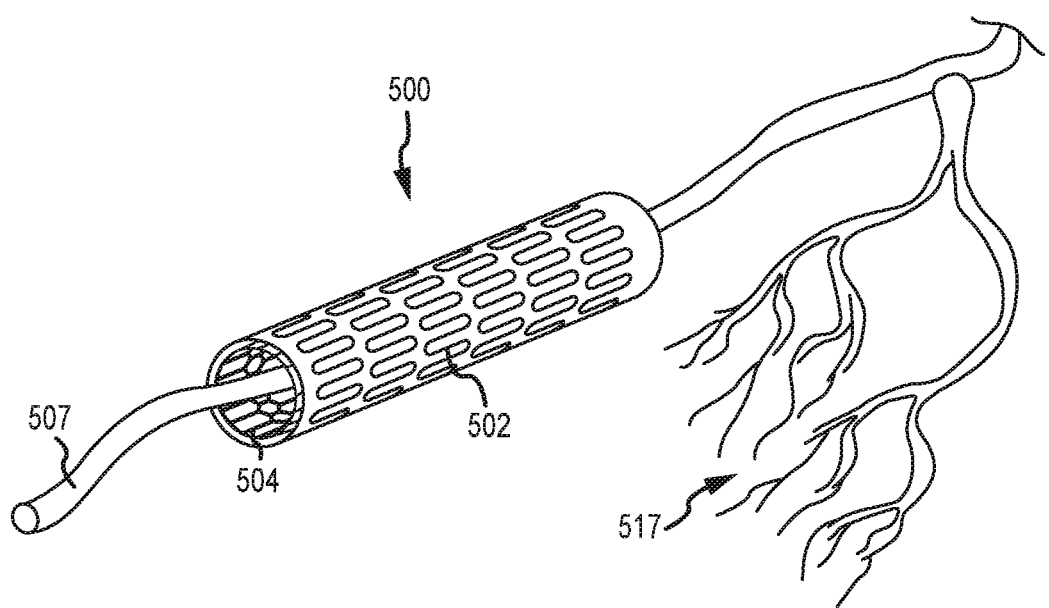
FIG. 5 illustrates a perspective view of an embodiment of a device in accordance with the present disclosure.

With reference now to FIG. 5, an exoluminal device 500, in accordance with the present disclosure, is illustrated. Device 500 is shown implanted within a body cavity, on an exterior portion of a vessel 507 within the vasculature 517. The illustration in FIG. 5 depicts an embodiment of a method of treatment for a body conduit, such as a vessel, and also depicts an embodiment of a method of maintaining a contractible implant 502 over-expanded around a body conduit for a predetermined period of time. The device 500 comprises a support structure 504 and a contractible implant 502 coaxially adjacent the support structure 504. Both the support structure 504 and implant 502 are substantially tubular in shape and approximately the same length, with the ends of each tubular component approximately aligned. In other embodiments, similar length components can not be aligned, and in other embodiments, the tubular lengths of the two components can differ such that one component can extend beyond the other at both ends. Upon bioabsorption of the support structure 504, the contractible implant will contract to its neutral state, which can result in constriction of a vessel, at least partially or completely.

Figure 6A:
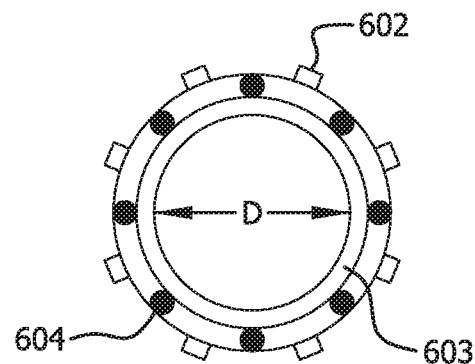
FIG. 6A illustrates a cross-sectional view of an embodiment of a device in accordance with the present disclosure surrounding a lumen.

With reference now to FIG. 6A, a cross-section of an implanted exoluminal device in accordance with the present disclosure is illustrated. The vessel 603 is circumferentially surrounded with an expandable implant 604 as described, which is coaxially adjacent a support structure 602. The inner surface of the device can have a layer that facilitates tissue in-growth. Expandable implant 604 is held in a constricted deformed configuration to allow for in-growth of tissue and eventually expand the vessel 603. Expandable implant 604 comprises a shape memory material allowing the implant 604 to expand back to a larger diameter when the support structure 602 is sufficiently bioabsorbed, resulting in dilation of the conduit, as discussed below. D is considered to be the "initial diameter."

Figure 6B:
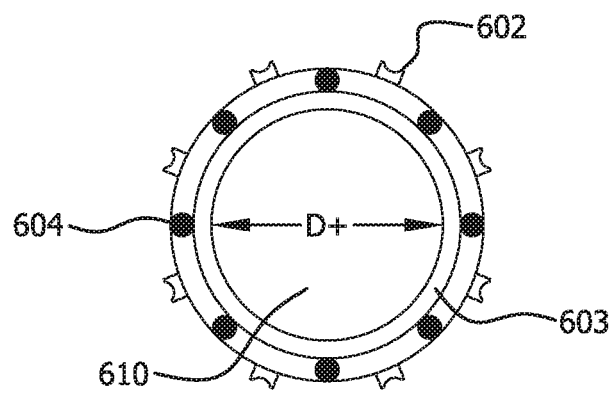
FIG. 6B illustrates a cross-sectional view of an embodiment of a device in accordance with the present disclosure partially constricting a lumen.

Referring now to FIG. 6B, a cross-section of the vessel 603 with a device in accordance with the present disclosure is illustrated. In this illustrated embodiment, the support structure 602 has partly bioabsorbed. As such, the self-expanding implant 604 has begun to expand and accordingly expand the conduit beneath it, as shown by the enlarged passageway 610. As discussed above, the support structure 602 may not be bioabsorbed uniformly, and as portions of the structure bioabsorbs, regions of the expandable implant 604 that are adjacent the support will begin to expand, whereas other portions of the implant 604 can remain structurally supported. Therefore, a cross-sectional view of the device in this result in the passageway 610 to be partially expanded as illustrated and depicted by D+.

Figure 6C:
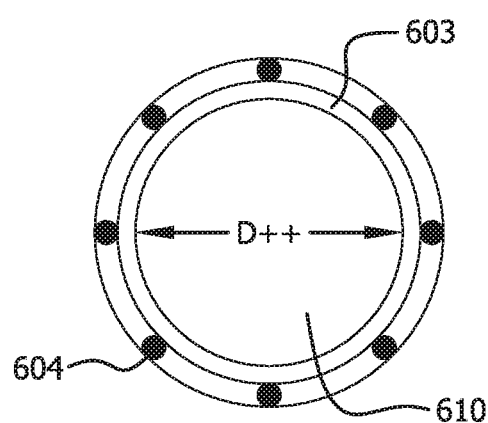
FIG. 6C illustrates a cross-sectional view of an embodiment of a device in accordance with the present disclosure constricting a lumen.

With reference now to FIG. 6C, a further state of a device in accordance with the present disclosure is illustrated, wherein the device has expanded a vessel 603 to a desired diameter, which is substantially the same as the neutral diameter of the implant. This expanded state occurs through in-growth or anchoring of the tissue, bioabsorption of the support structure, and the self-expansion of the implant 602. The host vessel diameter has now been "pulled" up to D++.

Figure 7A:
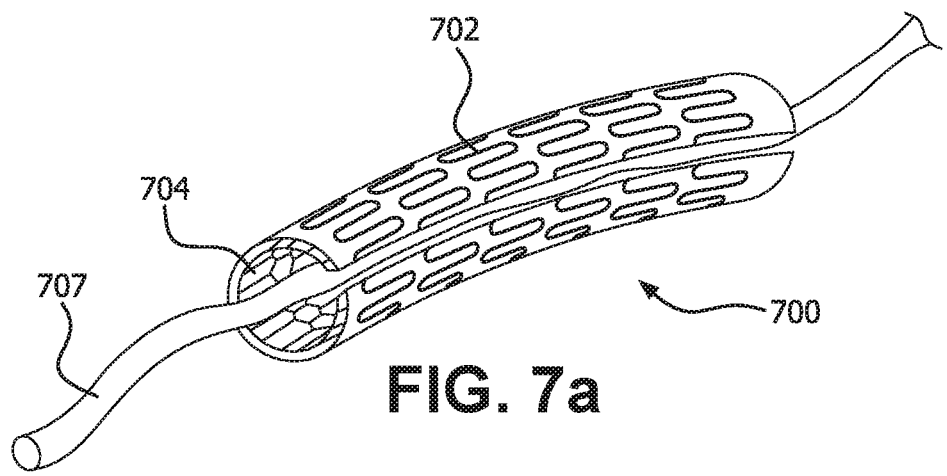
FIG. 7A illustrates a perspective view of an embodiment of a device in accordance with the present disclosure surrounding a vessel.

Referring now to FIG. 7A, an embodiment of an exoluminal device 700 comprising a discontinuous or an interlocking section along its length in accordance with the present disclosure is illustrated. As discussed above, the discontinuous or interlocking section along its length of the device 700 can be obtained by alignment of discontinuous or an interlocking section along its length present in both the support structure 704 and the implant 702. Implant 702 can be contractible or expandable as described herein. The opening allows the device 700 to be wrapped around the outside of a vessel 707 without a need to temporarily detach the vessel.

Figure 7B:
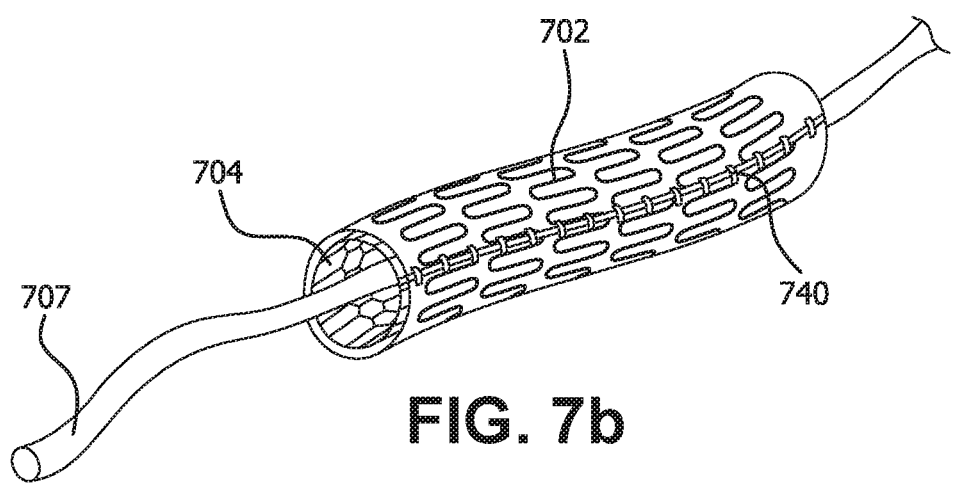
FIG. 7B illustrates a perspective view of an embodiment of a device in accordance with the present disclosure surrounding a vessel.

FIG. 7B is a perspective view of an exoluminal device that has been secured around a conduit such as a vessel in accordance with the present disclosure. The discontinuous section of the device can be closed with at least one suture 740. Interlacing the discontinuous section secures the device onto the vessel 707.

Figure 7C:
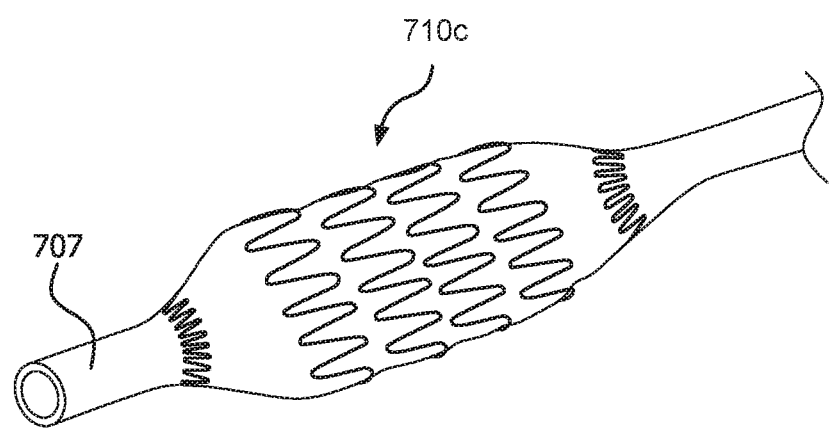
FIG. 7C illustrates a perspective view of an embodiment of a device in accordance with the present disclosure dilating a vessel.
Figure 7D:
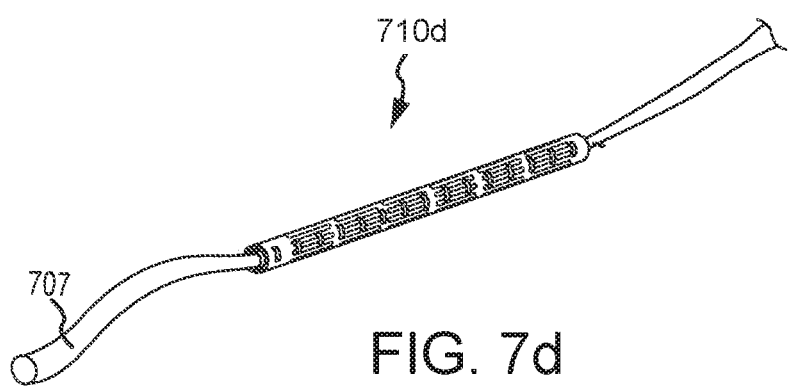
FIG. 7D illustrates a perspective view of an embodiment of a device in accordance with the present disclosure constricting a vessel.

Referring now to FIG. 7C, a perspective view of an expandable exoluminal device 710c in accordance with the present disclosure is illustrated. As shown, the device 710c has expanded the vessel 707 to a larger diameter Referring now to FIG. 7D, a perspective view of a contractible exoluminal device 710d in accordance with the present disclosure is illustrated. As shown, the device 710d has constricted the vessel 707 to a smaller diameter. A controlled constriction of vessel 707 can be used as a method for promoting collateral vascularization in a patient. Controlled constriction of the vessel 707 over a predetermined period of time can lead to collateral growth of vessels proximate the constriction without deleterious side effects.

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents.

Likewise, numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. A method of promoting collateral vascularization in a patient, the method comprising:

locating an implant in an over-expanded state around an exterior portion of a vessel, the implant including a support structure and a stent structure, the over-expanded state of the implant including the support structure being at a supporting diameter and the support structure supporting the stent structure at an expanded deformed diameter; and allowing the support structure to at least one of bio-corrode and structurally breakdown over time causing contraction of stent structure from the expanded deformed diameter to a contracted undeformed diameter, concomitant constriction of the vessel, and encouragement of collateral vascularization proximate to the vessel.

2. The method of claim 1, wherein fluid is permitted to flow through the vessel when the implant is in the over-expanded state and further wherein, upon contraction of the stent structure to the contracted, undeformed diameter the vessel is incapable of supporting fluid flow.

3. A method for maintaining an implant in an over-expanded state along a body lumen for a period of time, the method comprising:

locating an implant at a desired treatment location along the body lumen, the implant including a support structure and a stent structure;

expanding the support structure to an expanded supporting diameter resulting in radial expansion of the stent structure from a collapsed deformed diameter to an over-expanded deformed diameter at which the support structure supports the stent structure; and allowing the support structure to at least one of bio-corrode and structurally breakdown over the period of time such that the stent structure contracts from the over-expanded deformed diameter to a contracted, undeformed diameter over the period of time.

4. The method of claim 3, wherein locating the implant at a desired treatment location along the body lumen includes locating the implant within the body lumen with the support structure and the stent in a collapsed delivery configuration.

5. The method of claim 3, wherein fluid is permitted to flow through the body lumen when the stent is at the over-expanded deformed diameter and further wherein, after the stent structure contracts to the contracted, undeformed diameter the body lumen is incapable of supporting fluid flow.

6. The method of claims 3, wherein the desired treatment location is on the adventitia of a vessel within the vasculature of a patient.

7. A method for the controlled constriction of a vessel in a patient, the method comprising:

locating an implant in a starting configuration along the vessel, the implant including a support structure and a stent structure, the starting configuration comprising the support structure being at a supporting diameter maintaining the stent structure at an over-expanded deformed diameter; and allowing the support structure to at least one of bio-corrode and structurally breakdown controllably over time such that the stent structure returns toward an undeformed neutral diameter.

8. The method of claim 7, wherein allowing the support structure to at least one of bio-corrode and structurally breakdown results in contraction of the stent structure from the over-expanded deformed diameter to the undeformed neutral diameter.

9. The method of claim 7, wherein the support structure comprises a non-shape memory alloy that is biocorrodible.

10. The method of claim 7, wherein the support structure comprises a bio-corrodible metal alloy comprising an iron alloy.

11. The method of claim 7, wherein the support structure comprises a bio-corrodible metal alloy comprising an iron alloy having greater than at least one of about 50% iron, about 60% iron, about 70% iron, about 80% iron, about 90% iron, and about 95% iron.

12. The method of claim 7, wherein the support structure comprises a bio-corrodible metal alloy comprising: from 0 to about 40% manganese; 0 to about 5% chromium; 0 to about 10% nickel; 0 to about 25% cobalt; 0 to about 1% aluminum; 0 to about 5% molybdenum; 0 to about 3% titanium; 0 to about 3% zirconium; 0 to about 1% carbon; 0 to about 1% silicon; 0 to about 3% niobium; 0 to about 1% nitrogen; and 0 to about 1% yttrium, with the remainder being iron.

13. The method of claim 7, wherein the stent structure comprises a shape memory alloy.

14. The method of claim 7, wherein the stent structure comprises a Ni—Ti alloy.

15. The method of claim 7, wherein locating the implant in the starting configuration along the vessel includes radially expanding the support structure from a delivery collapsed diameter to the supporting diameter with a balloon.

16. The method of claim 15, wherein radial expansion of the support structure from the collapsed delivery diameter to the supporting diameter forces expansion of the stent structure to the over-expanded deformed diameter.

17. The method of claim 16, wherein the stent-structure is elastically biased to return from the over-expanded deformed diameter to the undeformed neutral diameter.

\* \* \* \* \*